(12) United States Patent
Vicic

(10) Patent No.: US 10,144,747 B2
(45) Date of Patent: Dec. 4, 2018

(54) REAGENTS AND METHODS FOR FLUORINATING A SUBSTRATE

(71) Applicant: Lehigh University, Bethlehem, PA (US)

(72) Inventor: David Vicic, Bethlehem, PA (US)

(73) Assignee: LEHIGH UNIVERSITY

( * ) Notice: Subject to any disclaimer, the term of this patent is extended or adjusted under 35 U.S.C. 154(b) by 0 days.

(21) Appl. No.: 14/903,724

(22) PCT Filed: Jul. 8, 2014

(86) PCT No.: PCT/US2014/045673
§ 371 (c)(1),
(2) Date: Jan. 8, 2016

(87) PCT Pub. No.: WO2015/006278
PCT Pub. Date: Jan. 15, 2015

(65) Prior Publication Data
US 2016/0176901 A1  Jun. 23, 2016

Related U.S. Application Data

(60) Provisional application No. 61/844,067, filed on Jul. 9, 2013.

(51) Int. Cl.
| | |
|---|---|
| *C07F 3/06* | (2006.01) |
| *C07D 215/18* | (2006.01) |
| *C07C 17/263* | (2006.01) |
| *C07F 15/04* | (2006.01) |

(52) U.S. Cl.
CPC .............. *C07F 3/06* (2013.01); *C07C 17/263* (2013.01); *C07D 215/18* (2013.01); *C07F 15/04* (2013.01); *C07C 2602/10* (2017.05)

(58) Field of Classification Search
CPC .......... C07F 3/06; C07F 15/04; C07C 17/263; C07C 2602/10; C07D 215/18
See application file for complete search history.

(56) References Cited

U.S. PATENT DOCUMENTS

| | | |
|---|---|---|
| 5,445,373 A | 8/1995 | Franks |
| 5,964,919 A | 10/1999 | Rieke |
| 2009/0118279 A1 | 5/2009 | Kokubo et al. |

OTHER PUBLICATIONS

International Search Report dated Oct. 9, 2014; International Application No. PCT/US2014/045673; International Filing Date: Jul. 8, 2014; 4 pages.
Written Opinion dated Oct. 9, 2014; International Application No. PCT/US2014/045673; International Filing Date: Jul. 8, 2014; 6 pages.

*Primary Examiner* — D Margaret M Seaman
(74) *Attorney, Agent, or Firm* — The Belles Group, P.C.

(57) ABSTRACT

Described herein are perfluoroalkylated zinc compounds having the structure of Formula (I) or Formula (II), which can be used to perfluoroalkylate organic, inorganic and organometallic substrates. Methods of making and using these compounds by reacting zinc or a dialkylzinc compound with a perfluoroalkyl dihalide in a solvent such as tetrahydrofuran, dioxane or diglyme, are also described.

13 Claims, No Drawings

REAGENTS AND METHODS FOR FLUORINATING A SUBSTRATE

CROSS-REFERENCE TO RELATED APPLICATION

This application claims priority to U.S. Provisional Application Ser. No. 61/844,067, filed 9 Jul. 2013, entitled "REAGENTS AND METHOD FOR $(CF_2)_n$ TRANSFER THAT ELIMINATE USE OF HAZARDOUS FLUORINE GASES", the entirety of which is hereby incorporated herein.

STATEMENT OF GOVERNMENT INTEREST

This invention was made with government support under the Office of Basic Energy Sciences of the U.S. Department of Energy (DE-FG02-13ER16369). The government has certain rights in the invention.

BACKGROUND

Fluorinated compounds are found in a diverse array of products, e.g. refrigerants, gaskets, pharmaceuticals, pesticides, surfactants, polymers, liquid crystals, anesthetics, blood substitutes, aerosol formulations and lubricants. However, conventional methods of fluorinating compounds involve the use of hazardous gases, e.g. tetrafluoroethylene (TFE). The hazardous nature of these gases has become problematic for discovery research, as gases such as TFE have become increasingly unavailable due to the risk associated with their handling.

Despite the fact that TFE can be prepared rather inexpensively on a reasonable scale from the thermal pyrolysis of waste polytetrafluoroethylene (PTFE), the synthetic route requires temperatures in excess of 600° C. and the use of a quartz furnace connected to a vacuum manifold. Moreover, the pyrolysis route does not eliminate the detonation hazards accompanying the re-condensed TFE or the problems associated with the acute toxicity of octoflurorisobutylene, which can be formed as a byproduct in the thermal degradation of PTFE.

Other methods exist which provide TFE more expensively on a small scale; however, these methods require gas handling techniques which can complicate experimental protocols.

Thus, there remains a need for reagents which are capable of fluorinating a substrate, without the explosion hazards and toxicity associated with existing materials, methods and devices. Embodiments of the present invention are directed to meeting these needs.

SUMMARY

In some embodiments, the present invention provides a compound of Formula (I):

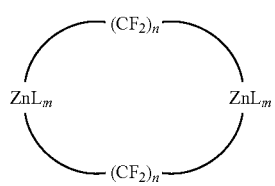

(I)

wherein:
  n is an integer ranging from 2 to 6;
  L comprises tetrahydrofuran; dioxane; acetonitrile; diethyl ether; N-methylmorpholine; triethylamine; dimethoxyethane; bipyridine; N,N,N',N'-tetramethylethylenediamine; N,N,N',N'-tetraethylethylenediamine; a glyme-type solvent; or 1,3-dimethyl-3,4,5,6-tetrahydro-2(1H)-pyrimidinone; and
  m is an integer ranging from 1 to 3.

Other embodiments provide a composition of Formula (II)

$$(Y)_m(X)_q Zn-(CF_2)_p-Zn(X)_q(Y)_m \qquad (II)$$

wherein:
  p is an integer ranging from 2 and 12;
  Y comprises tetrahydrofuran; dioxane; acetonitrile; diethyl ether; N-methylmorpholine; triethylamine; dimethoxyethane; bipyridine; N,N,N',N'-tetramethylethylenediamine; N,N,N',N'-tetraethylethylenediamine; a glyme-type solvent; or 1,3-dimethyl-3,4,5,6-tetrahydro-2(1H)-pyrimidinone;
  m is an integer ranging from 1 to 3;
  each X is independently selected from Br; I; Cl; tosylate; mesylate; and $CF_3SO_3^-$; and
  q is an integer ranging from 1 to 2.

Further embodiments provide a method for preparing a compound of Formula (I):

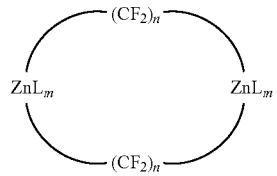

(I)

wherein:
  n is an integer ranging from 2 to 6;
  L comprises tetrahydrofuran; dioxane; acetonitrile; diethyl ether; N-methylmorpholine; triethylamine; dimethoxyethane; bipyridine; N,N,N',N'-tetramethylethylenediamine; N,N,N',N'-tetraethylethylenediamine; a glyme-type solvent; or 1,3-dimethyl-3,4,5,6-tetrahydro-2(1H)-pyrimidinone; and
  m is an integer ranging from 1 to 3; the method comprising:
    reacting a compound of Formula (III):

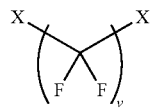

(III)

wherein v is an integer ranging from 2 to 6;
  with a compound of Formula (IV):

$$Zn(R^a)_2 \qquad (IV)$$

in the presence of a solvent;
wherein
  each X is independently selected from Br; I; Cl; tosylate; mesylate; and $CF_3SO_3^-$; and
  $R^a$ is $C_1$-$C_{10}$ alkyl.

Further embodiments provide a method for preparing a compound of Formula (II):

$$(Y)_m(X)_q Zn\text{—}(CF_2)_p\text{—}Zn(X)_q(Y)_m \quad (II)$$

wherein:
p is an integer ranging from 2 to 12;
Y comprises tetrahydrofuran; dioxane; acetonitrile; diethyl ether; N-methylmorpholine; triethylamine; dimethoxyethane; bipyridine; N,N,N',N'-tetramethylethylenediamine; N,N,N',N'-tetraethylethylenediamine; a glyme-type solvent; or 1,3-dimethyl-3,4,5,6-tetrahydro-2(1H)-pyrimidinone;
m is an integer ranging from 1 to 3;
q is an integer ranging from 1 to 2; and
each X is independently selected from Br; I; Cl; tosylate; mesylate; and $CF_3SO_3^-$; the method comprising reacting a compound of Formula (III):

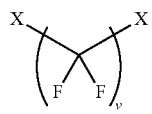
(III)

with a zinc metal in the presence of a solvent;
wherein:
v is an integer ranging from 2 to 12; and
each X is independently selected from Br; I; Cl; tosylate; mesylate; and $CF_3SO_3^-$.

DETAILED DESCRIPTION

As used herein, the term "reacting" refers to the bringing together of designated chemical reactants such that a chemical transformation takes place generating a compound different from any initially introduced into the system. Reacting can take place in the presence or absence of solvent.

As used herein, "alkyl", "alkylenyl" or "alkylene" used alone or as a suffix or prefix, is intended to include both branched and straight-chain saturated aliphatic hydrocarbon groups having from 1 to 12 carbon atoms or if a specified number of carbon atoms is provided then that specific number would be intended. For example "$C_{1-6}$ alkyl" denotes alkyl having 1, 2, 3, 4, 5 or 6 carbon atoms. Examples of alkyl include, but are not limited to, methyl, ethyl, n-propyl, propyl, n-butyl, i-butyl, sec-butyl, t-butyl, pentyl, and hexyl, or any subset thereof. As used herein, "$C_{1-3}$ alkyl", whether a terminal substituent or an alkylene (or alkylenyl) group linking two substituents, is understood to specifically include both branched and straight-chain methyl, ethyl, and propyl.

As used herein, the term "heterocyclyl" or "heterocyclic" or "heterocycle" refers to ring-containing monovalent and divalent structures having one or more heteroatoms, independently selected from N, O and S, as part of the ring structure and comprising from 3 to 20 atoms in the rings, or 3- to 7-membered rings. Heterocyclic groups may be saturated or partially saturated or unsaturated, containing one or more double bonds, and heterocyclic groups may contain more than one ring as in the case of polycyclic systems. The heterocyclic rings described herein may be substituted on carbon or on a heteroatom atom if the resulting compound is stable. If specifically noted, nitrogen in the heterocyclyl may optionally be quaternized. It is understood that when the total number of S and O atoms in the heterocyclyl exceeds 1, then these heteroatoms are not adjacent to one another.

Examples of heterocycles include, hut are not limited to, 1H-indazole, 2-pyrrolidonyl, 2H, 6H-1, 5,2-dithiazinyl, 2H-pyrrolyl, 3H-indolyl, 4-piperidonyl, 4aH-carbazole, 4H-quinolizinyl, 6H-1, 2,5-thiadiazinyl, acridinyl, azabicyclo, azetidine, azepane, aziridine, azocinyl, benzimidazolyl, benzodioxol, benzofuranyl, benzothiofuranyl, benzothiophenyl, benzoxazolyl, benzthiazolyl, benzotriazolyl, benzotetrazolyl, benzisoxazolyl, benzisothiazolyt, benzimidazalonyl, carbazolyl, 4aH-carbazolyl, b-carbolinyl, chromanyl, chromenyl, cinnolinyl, diazepane, decahydroquinolinyl, 2H,6H-1,5,2-dithiazinyl, dioxolane, furyl, 2,3-dihydrofuran, 2,5-dihydrofuran, dihydrofuro[2,3-b]tetrahydrofuran, furanyl, furazanyl, homopiperidinyl, imidazolidine, imidazolidinyl, imidazolinyl, imidazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, ,1,2,3-oxadiazolyl, 1,2,4-oxadiazolyl, 1,2,5-oxadiazolyl, 1,3,4-oxadiazolyl, oxazolidinyl, oxazotyl, oxirane, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, purinyl, pyranyi, pyrrolidinyl, pyrroline, pyrrolidine, pyrazinyl, pyrazolidinyl, pyrazolinyl, pyrazolyi, pyridazinyl, pyridooxazole, pyridoimidazole, pyridothiazole, pyridinyl, N-oxide-pyridinyl, pyridyl, pyrimidinyl, pyrrolidinyl, pyrrolidinyl dione, pyrrolinyl, pyrrolyl, pyridine, quinazolinyl, quinolinyl, 4H-quinoxalinyl, quinuclidinyl, carbolinyl, tetrahydrofuranyl, tetramethylpiperidinyl, tetrahydroquinoline, tetrahydroisoquinolinyl, thiophane, thiotetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazotyl, thienooxazolyl, thienoimidazolyl, thiopheneyl, thiirane, triazinyl, 1,2,3-triazolyi, 1,2,4-triazolyl, 1,2,5-triazolyl, 1,3,4-triazolyl, and xanthenyl, or any subset thereof.

As used herein, "halo" or "halogen" includes fluoro, chloro, bromo, and iodo, or any subset thereof.

In some embodiments, the present invention relates to new (perfluoroalkyl)metallacyclic zinc reagents.

In some embodiments, the (perfluoroalkyl)metallacyclic zinc compounds of the present invention comprise the structure of Formula (I):

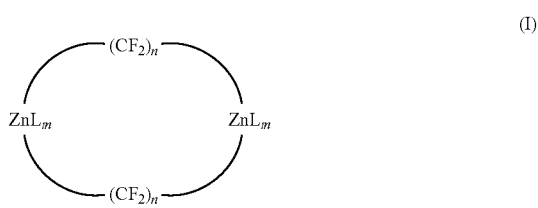
(I)

wherein:
n is an integer ranging from 2 to 6; and
m is an integer ranging from 1 to 3.

In some embodiments, n is 2. In some embodiments, n is 3. In some embodiments, n is 4. In some embodiments, n is 5. In some embodiments, n is 6. In some embodiments, m is 1. In some embodiments, m is 2. In some embodiments, m is 3.

In some embodiments, L is a ligand that is a reaction product of one or more compounds selected from: tetrahydrofuran; dioxane; acetonitrile; diethyl ether; N-methylmorpholine; triethylamine; dimethoxyethane; bipyridine; N,N,N',N'-tetramethylethylenediamine; N,N,N',N'-tetraethylethylenediamine; a glyme-type solvent; and 1,3-Dimethyl-3,4,5,6-tetrahydro-2(1H)-pyrimidinone.

In some embodiments, the ligand is a reaction product of a glyme-type solvent having the formula: $CH_3O(CH_2CH_2O)_tCH_3$; wherein t is an integer ranging from 1 to 10. In some embodiments, the ligand is a reaction product of diethylene glycol dimethyl ether.

In some embodiments, the compound of Formula (I) may be produced by reacting a compound of Formula (III):

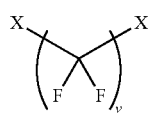

(III)

wherein v is an integer ranging from 2 to 6;
with a compound of Formula (IV):

(IV)

wherein $R^a$ is $C_1$-$C_{10}$ alkyl;
and a third reactant.

In some embodiments, v is an integer ranging from 2 to 4. In some embodiments, v is 2. In some embodiments, v is 3. In some embodiments, v is 4. In some embodiments, v is 5. In some embodiments, v is 6.

In some embodiments, each X is independently selected from Br; I; Cl; tosylate; mesylate; and $CF_3SO_3^-$.

In some embodiments, $R^a$ is a $C_1$-$C_{10}$ alkyl. In some embodiments, $R^a$ is selected from methyl, ethyl, propyl, butyl, pentyl, hexyl, heptyl, octyl, nonyl, decyl, isopropyl, and sec-butyl.

In some embodiments, the third reactant reacts to form a ligand, the third reactant being selected from: tetrahydrofuran; dioxane; acetonitrile; diethyl ether; N-methylmorpholine; triethylamine; dimethoxyethane; bipyridine; N,N,N',N'-tetramethylethylenediamine; N,N,N',N'-tetraethylethylenediamine; a glyme-type solvent; and 1,3-Dimethyl-3,4,5,6-tetrahydro-2(1H)-pyrimidinone.

In some embodiments, the third reactant reacts to form a ligand, the third reactant being a glyme-type solvent having the formula $CH_3O(CH_2CH_2O)_tCH_3$; wherein t is an integer ranging from 1 to 10. In some embodiments, the third reactant may be diethylene glycol dimethyl ether.

In some embodiments, the reaction of a compound of Formula (III), a compound of Formula (IV), and a third reactant may take place in a solvent. In some embodiments, the solvent may be a $C_5$-$C_8$ alkane. In some embodiments, the solvent may be a hexane, selected from n-hexane; cyclohexane; 2-methylpentane; 3-methyl pentane; 2,3-dimethylbutane; and 2,2-dimethybutane, as well as pentane; octane; and heptane.

In some embodiments, a compound of Formula (III), a compound of Formula (IV), and the third reactant may each be individually pre-dissolved in solvent before being added to a reaction mixture. In some embodiments, a compound of Formula (III), a compound of Formula (IV), and a third reactant may each be individually pre-chilled before being added to a reaction mixture.

In some embodiments, the present invention provides a compound having the structure of Formula (II):

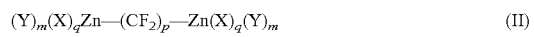

(II)

wherein:
p is an integer ranging from 2 to 12;
q is an integer ranging from 1 to 2; and
m is an integer ranging from 1 to 3.

In some embodiments, p is an integer ranging from 4 to 8. In some embodiments, p is an integer ranging from 3 to 5. In some embodiments, p is 4. In some embodiments, p is 6. In some embodiments, p is 8. In some embodiments, p is 10. In some embodiments, p is 12. In some embodiments, m is 1. In some embodiments, m is 2. In some embodiments, m is 3.

In some embodiments, Y is a ligand that is the reaction product of a compound selected from: tetrahydrofuran; dioxane; acetonitrile; diethyl ether; N-methylmorpholine; triethylamine; dimethoxyethane; bipyridine; N,N,N',N'-tetramethylethylenediamine; N,N,N',N'-tetraethylethylenediamine; a glyme-type solvent; and 1,3-Dimethyl-3,4,5,6-tetrahydro-2(1H)-pyrimidinone.

In some embodiments, Y is a ligand that is the reaction product of a glyme-type solvent and has the formula: $CH_3O(CH_2CH_2O)_tCH_3$; wherein t is an integer from 1 to 10. In some embodiments, Y is a ligand produced from diethylene glycol dimethyl ether.

In some embodiments, X is selected from: Br; I; Cl; tosylate; mesylate; and $CF_3SO_3^-$.

In some embodiments, the compound of Formula (II) may be produced by reacting a compound of Formula (III):

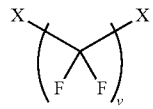

(III)

with a zinc metal; and
a reactive solvent.

In some embodiments, v is an integer ranging from 2 to 12. In some embodiments, v is an integer ranging from 4 to 8. In some embodiments, v is an integer ranging from 3 to 5. In some embodiments, v is 2. In some embodiments, v is 3. In some embodiments, v is 4. In some embodiments, v is 5. In some embodiments, v is 6. In some embodiments, v is 7. In some embodiments, v is 8. In some embodiments, v is 9. In some embodiments, v is 10. In some embodiments, v is 11. In some embodiments, v is 12.

In some embodiments, each X is independently selected from Br; I; Cl; tosylate; mesylate; and $CF_3SO_3$.

In some embodiments, the reactive solvent reacts to produce the ligand (Y) of Formula (II). In some embodiments, one or a mixture of two or more different reactive solvents may be used in the reaction mixture.

In some embodiments, a first reactive solvent may be included in the reaction mixture of the compound of Formula (III) and the zinc metal, resulting in a reaction product that exhibits a first ligand (Y) on a compound of Formula (II). In some embodiments, a second reactive solvent may then be added to the compound of Formula (II) having the first ligand (Y), wherein the second reactive solvent reacts to form second ligand groups that replace one or more of the first ligands on the compound of Formula (II), as demonstrated in Scheme II, wherein r is an integer ranging from 1 to 3.

In some embodiments, the reactive solvent is selected from: tetrahydrofuran; dioxane; acetonitrile; diethyl ether; N-methylmorpholine; triethylamine; dimethoxyethane; bipyridine; N,N,N',N'-tetramethylethylenediamine; N,N,N',N'-tetraethylethylenediamine; a glyme-type solvent; and 1,3-Dimethyl-3.4,5,6-tetrahydro-2(1H)-pyrimidinone.

In some embodiments, the reactive solvent is a glyme-type solvent and has a formula: $CH_3O(CH_2CH_2O)_tCH_3$; wherein t is an integer ranging from 1 to 10. In some embodiments, the third reactant may be diethylene glycol dimethyl ether.

In some embodiments, the compound of Formula (II) may be produced in the presence of an inert solvent. In some embodiments, the inert solvent may be a $C_5$-$C_8$ alkane. In some embodiments, the inert solvent may be a hexane, selected from n-hexane; cyclohexane; 2-methylpentane; 3-methyl pentane; 2,3-dimethylbutane; and 2,2-dimethybutane, pentane; octane; and heptane.

In some embodiments, the compound of Formula (III), the zinc metal, and the reactive solvent may each be pre-chilled before being added to the reaction mixture. In some embodiments, the inert solvent may be added to each reactant prior to being mixed together in the reaction mixture. In some embodiments, the inert solvent may be added to the reaction mixture after the reaction.

In some embodiments, the compounds of the present invention may be used to fluorinate an organic, inorganic or organometallic substrate. In some embodiments, the fluorination of a substrate comprises reacting a compound of Formula (I) or Formula (II) with a halogenated nickel compound. In some embodiments, the halogenated nickel compound is $NiBr_2$. In some embodiments, the fluorination of a substrate comprises reacting a compound of Formula (I) or Formula (II) with a halogenated heterocyclic compound. In some embodiments, the heterocyclic compound is a monocyclic or bicyclic 5-12 membered heterocyclic compound. In some embodiments, the heterocyclic compound is selected from a pyrrolidine, a pyrole, a piperidine, a pyridine, an azepane, an azepine, an indole, a quinolone, a benzazepine, and a carbazole. In some embodiments, the halogenated heterocyclic compound is 2,3-diiodopyridine.

According to some embodiments, the compounds or the present invention provide a cheaper and safer method to fluorinate various substrates.

Given the importance of transmetalation reactions in synthetic chemistry, some embodiments of the present invention provide an advantage over known fluorinating agents, as well as their method of production because the present invention eliminates the need for TFE or reclaimed TFE from PTFE when making the (perfluoroalkyl)metallacyclic zinc compounds of the present invention. In some embodiments, the (perfluoroalkyl)metallacyclic zinc compounds of the present invention result in air-stable, free-flowing solids that avoid the explosive hazards associated with conventional methods of fluorinating substrates. By eliminating the need for TFE or reclaimed TFE from PTFE, the present invention reduces cost and risk while also increasing the availability of resources needed to conduct traditional synthetic laboratory research.

Additionally, some embodiments provide that the compounds of the present invention may be used to produce products for a diverse set of industries, including, but not limited to, fluorinated refrigerants, gaskets, pharmaceuticals, pesticides, surfactants, polymers, liquid crystals, anesthetics, blood substitutes, aerosol formulations and lubricants.

Compounds of the present invention can be prepared, for example, using the reaction pathways and techniques as described below in Schemes I and II:

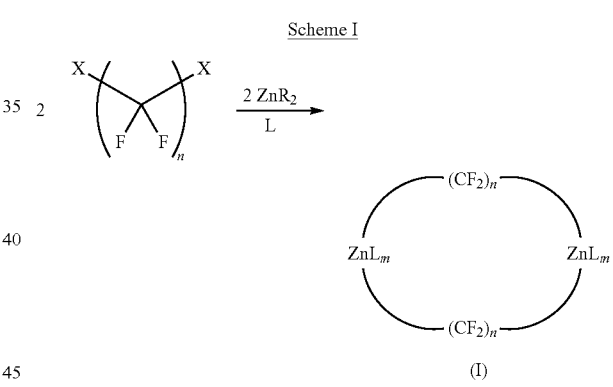

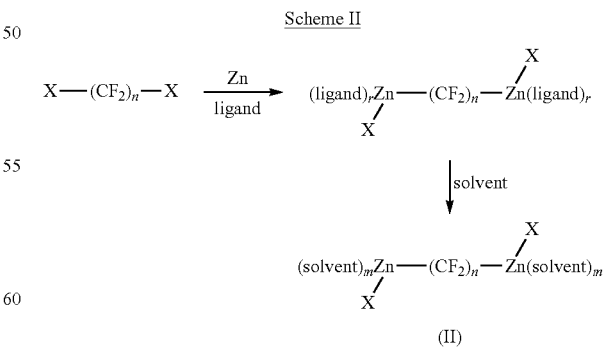

In some embodiments, for example, as shown in Scheme II (above), r is an integer ranging from 1 to 3. In some embodiments, r is 1. In some embodiments, r is 2. In other embodiments, r is 3.

The invention will be described in greater detail by way of specific examples. The following examples are offered for illustrative purposes and are not intended to limit the invention in any manner. Those skilled in the art will readily recognize a variety of noncritical parameters, which can be changed or modified to yield essentially the same results.

EXAMPLES

Example 1

Preparation of an Exemplary (perfluoroalkyl)metallacyclic Zinc Compound

Eight (8) mL of 1.0M diethyl zinc solution is pre-chilled to (−)78° C.) under nitrogen atmosphere. 3.64 grams of 1,4-diiodooctafluorobutane in 10 mL of pentane is also chilled to (−) 78° C. The zinc solution is added drop-wise to the alkyl halide and stirred at (−)20° C. for 3 hours. The solution is then warmed to room temperature and stirred vigorously with 4 mL of MeCN for 10 hours. The solution is then pumped dry on a high vacuum line. The resulting solid is dissolved in 10 mL of acetonitrile, filtered, and pumped dry again. Yield: 85.6%. $^{1}$H NMR $CD_3CN$ (500 MHz): 1.95 (s). $^{19}$F NMR data for $[(MeCN)_2Zn(C_4F_8)]$ in $CD_3CN$ (470 MHz): δ −125.5 (br s), −125.8 (br s).

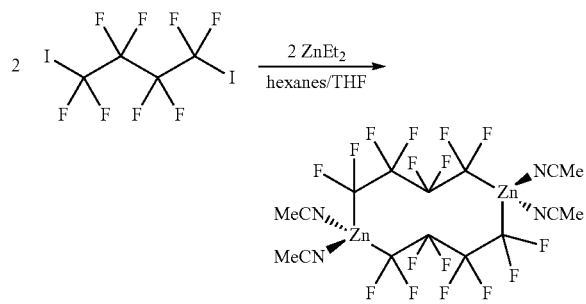

Example 2

Preparation of $(diglyme)BrZn(CF_2)_4ZnBr(diglyme)$

To a resealable pressure tube is added Zn dust (0.3925 g, 6 mmol), and a solution of $Br(CF_2)_4Br$ (1.2604 g, 3.5 mmol) in diglyme (4 mL) under nitrogen atmosphere at room temperature. The resulting mixture is sealed and quickly submerged in an oil bath preheated to 100° C. After 20 mins, the mixture is cooled to room temperature, diluted with 4 mL of pentane and filtered under $N_2$ atmosphere to afford dizincbromide diglyme complex (1.7237 g, 76%): grey solid. $^{19}$F NMR of solid in THF-$d_8$ (471 MHz, THF-$d_8$) δ −122.52 (s, 4F), −124.27 (s, 4F). Anal. Calcd (found) for $C_{16}H_{28}Br_2F_8O_6Zn_2$: C, 25.32 (23.50); H, 3.72 (3.60). Recrystallization from THF/Pentane affords X-ray quality crystals of $[(THF)_2BrZn(CF_2)_4ZnBr(THF)_2]$.

Example 3

Preparation of $(MeCN)_2Ni(C_4F_8)$

[(dimethoxyethane)NiBr$_2$] (30.9 mg, 0.1 mmol), and diz-incbromide diglyme complex (151.8 mg, 0.2 mmol) are dissolved in 2 mL of MeCN and stirred for 3 hours at room temperature in a glovebox, and then the volatiles are removed under vacuum. The nickel complex is extracted from the residue with benzene, and this benzene solution is filtered then dried under vacuum to yield a yellow solid (289.7 mg, 85%). $^{19}$F NMR ($CD_3CN$, 470 MHz): δ −107.36 (s, 4F), −140.13 (s, 4F). The reaction is described below in Scheme IV:

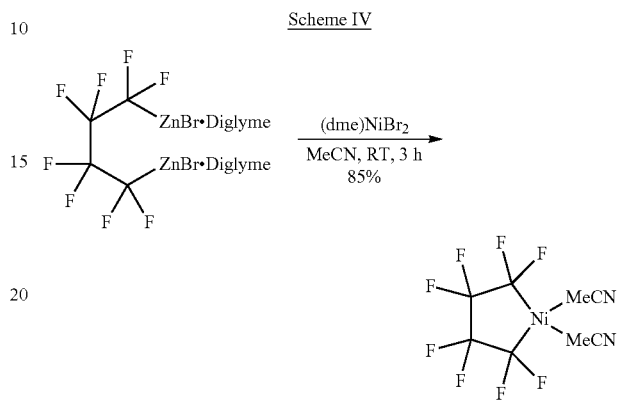

Example 4

Preparation of 5,5,6,6,7,7,8,8-octafluoro-5,6,7,8-tetrahydroquinoline from a diglyme zinc Complex To a resealable pressure tube is added the zinc complex (151.8 mg, 0.2 mmol), copper chloride (19.4 mg, 0.2 mmol), 2,3-diiodopyridine (33.1 mg, 0.1 mmol), 1 mL of DMF under $N_2$ atmosphere at room temperature. The resulting mixture is sealed and quickly submerged in an oil bath preheated to 100° C. After 17 h, the mixture is cooled to room temperature and 0.012 mL of trifluorotoluene (0.098 mmol) is syringed into the tube as the internal standard. The NMR yield of 5,5,6,6,7,7,8,8-octafluoro-5,6,7,8-tetrahydroquinoline is 75%. $^{19}$F NMR ($CDCl_3$, 470 MHz): δ −105.9 (s, 2F), −111.2 (s, 2F), −135.6 (s, 2F), −136.0 (s, 2F). The reaction is described below in Scheme V:

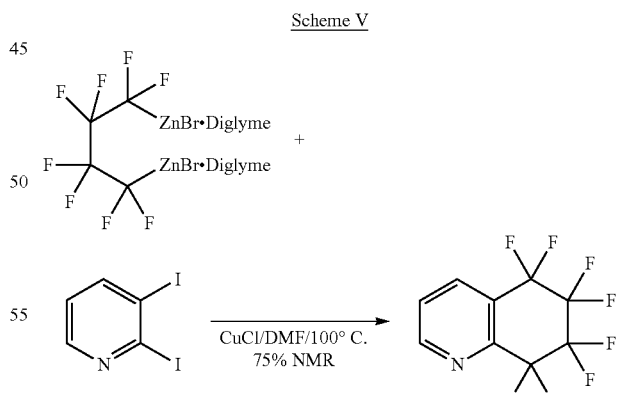

Example 5

Products Prepared by an Exemplary perfluorometallacyclopentane Derivative

Scheme VI (below) describes a few examples of products that could be made with an exemplary reagent of the present invention, wherein M is a metal, e.g. nickel.

Scheme VI

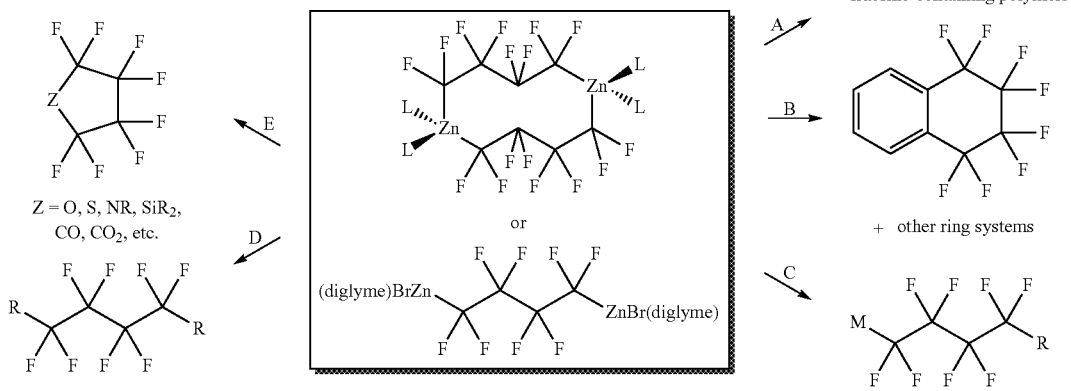

It is intended that any patents, patent applications or printed publications, including books, mentioned in this patent document be hereby incorporated by reference in their entirety.

As those skilled in the art will appreciate, numerous changes and modifications may be made to the embodiments described herein, without departing from the spirit of the invention. It is intended that all such variations fall within the scope of the invention.

The invention claimed is:

1. A compound of formula (I):

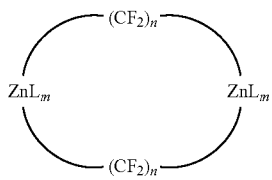 (I)

wherein:
n is an integer ranging from 2 to 6;
L is selected from one or more of tetrahydrofuran; dioxane; acetonitrile; diethyl ether; N-methylmorpholine; triethylamine; bipyridine; N,N,N',N'-tetramethylethylenediamine; N,N,N',N'-tetraethylethylenediamine; a glyme; or 1,3-dimethyl-3,4,5,6-tetrahydro-2(1H)pyrimidinone; and
m is an integer ranging from 1 to 3.

2. The compound of claim 1, wherein n is 4.

3. The compound of claim 1, wherein the glyme has the following formula: $CH_3O(CH_2CH_2O)_tCH_3$; wherein t is an integer between 1 and 10.

4. The compound of claim 1, wherein the glyme is diethylene glycol dimethyl ether.

5. A method for preparing a compound of formula (I):

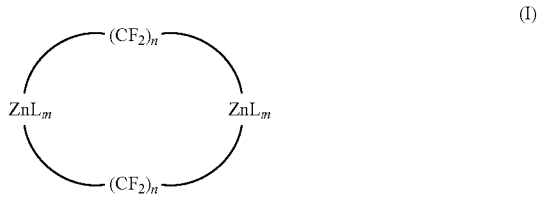 (I)

wherein:
n is an integer ranging from 2 to 6;
L is selected from one or more of tetrahydrofuran; dioxane; acetonitrile; diethyl ether; N-methylmorpholine; triethylamine; bipyridine; N,N,N',N'-tetramethylethylenediamine; N,N,N',N'-tetraethylethylenediamine; a glyme; or 1,3-dimethyl-3,4,5,6-tetrahydro-2(1H)pyrimidinone; and
m is an integer ranging from 1 to 3; the method comprising:
reacting a compound of Formula (III):

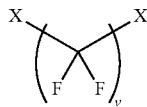 (III)

wherein v is an integer ranging from 2 to 6;
with a compound of Formula (IV):

$$Zn(R^a)_2 \quad (IV)$$

in the presence of a solvent;
wherein:
each X is independently selected from Br; I; Cl; tosylate; mesylate; and $CF_3SO_3^-$; and
$R^a$ is $C_1$-$C_{10}$ alkyl.

6. The method of claim 5, wherein the solvent comprises a $C_5$-$C_8$ alkyl compound.

7. The method of claim 5, wherein the solvent comprises a hexane selected from n-hexane; 2-methylpentane; 3-methylpentane; 2,3-dimethylbutane; and 2,2-dimethylbutane.

8. A method of fluorinating a substrate comprising:
reacting a compound according to claim 1 with a halogenated nickel compound.

9. The method of claim 8, wherein the halogenated nickel compound is NiBr$_2$.

10. A method of fluorinating a substrate comprising:
   reacting a compound according to claim 1 with a halogenated heterocylic compound.

11. The method of claim 10, wherein the heterocylic compound is a monocyclic or bicyclic 5-12 membered heterocyclic compound.

12. The method of claim 10, wherein the heterocylic compound is selected from a pyrrolidine, a pyrole, a piperidine, a pyridine, an azepane, an azepine, an indole, a quinoline, a benzazepine, and a carbazole.

13. The method of claim 10, wherein the halogenated heterocyclic compound is 2,3-diiodopyridine.

* * * * *